United States Patent
Hashimoto

(10) Patent No.: US 11,551,354 B2
(45) Date of Patent: Jan. 10, 2023

(54) INTERLOBAR MEMBRANE DISPLAY APPARATUS, METHOD, AND PROGRAM

(71) Applicant: FUJIFILM Corporation, Tokyo (JP)

(72) Inventor: Takayuki Hashimoto, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 69 days.

(21) Appl. No.: 16/935,171

(22) Filed: Jul. 21, 2020

(65) Prior Publication Data
US 2020/0349703 A1    Nov. 5, 2020

Related U.S. Application Data

(63) Continuation of application No. PCT/JP2018/042896, filed on Nov. 20, 2018.

(30) Foreign Application Priority Data

Jan. 30, 2018 (JP) .............................. JP2018-013432

(51) Int. Cl.
    *G06T 7/00*      (2017.01)

(52) U.S. Cl.
CPC .. *G06T 7/0012* (2013.01); *G06T 2207/10081* (2013.01); *G06T 2207/10088* (2013.01); *G06T 2207/30061* (2013.01); *G06T 2207/30096* (2013.01)

(58) Field of Classification Search
CPC ......... G06T 7/0012; G06T 2207/10081; G06T 2207/10088; G06T 2207/30061; G06T 2207/30096; G06T 2219/016; G16H 30/40
See application file for complete search history.

(56) References Cited

U.S. PATENT DOCUMENTS

| 9,014,445 B2 | 4/2015 | Yin et al. |
| 2014/0105472 A1* | 4/2014 | Yin ........................ G06T 7/0012 382/128 |
| 2015/0187118 A1* | 7/2015 | Masumoto .............. G06T 15/08 345/419 |
| 2018/0047168 A1* | 2/2018 | Chen ......................... G06T 7/11 |

FOREIGN PATENT DOCUMENTS

| JP | 2008142481 | 6/2008 |
| JP | 2009273644 | 11/2009 |
| JP | 2014161388 | 9/2014 |

OTHER PUBLICATIONS

"Office Action of Japan Counterpart Application", dated Feb. 16, 2021, with English translation thereof, p. 1-p. 4.

(Continued)

*Primary Examiner* — Vu Le
*Assistant Examiner* — Winta Gebreslassie
(74) *Attorney, Agent, or Firm* — JCIPRNET

(57) ABSTRACT

An interlobar position specifying unit specifies an interlobar position in a lung field area included in a three-dimensional image. An expansion unit expands a plane area at the interlobar position in a thickness direction to generate an expansion area including an interlobar membrane. A projection processing unit processes the expansion area by a projection method that emphasizes the interlobar membrane to generate a projection image. The display control unit displays the projection image on a display.

8 Claims, 10 Drawing Sheets

(56) References Cited

OTHER PUBLICATIONS

T. Hayashi, et al., "Development of the Procedure for Automatic Extracting Interlobar Fissures and its Performance Evaluation," Technical Report of IEICE, Oct. 2003, pp. 39-44.
"International Search Report (Form PCT/ISA/210) of PCT/JP2018/042896," dated Feb. 19, 2019, with English translation thereof, pp. 1-5.
"Written Opinion of the International Searching Authority (Form PCT/ISA/237) of PCT/JP2018/042896," dated Feb. 19, 2019, with English translation thereof, pp. 1-7.
Anle Yu, et al., "Conditions and Mechanism for the Appearance of Interlobar Fissures as 5-Line Signs in Axial Maximum Intensity Projection Images," Journal of Computer Assisted Tomography, vol. 38, Aug. 2014, pp. 578-585.
Ue Hidenori, et al., "Extraction of Lung Lobes in X-ray CT Images," Medical Imaging Technology, vol. 21, Mar. 2003, pp. 122-130.

* cited by examiner

INTERLOBAR MEMBRANE DISPLAY APPARATUS, METHOD, AND PROGRAM

CROSS REFERENCE TO RELATED APPLICATIONS

The present application is a Continuation of PCT International Application No. PCT/JP2018/042896 filed on Nov. 20, 2018, which claims priority under 35 U.S.C. § 119(a) to Japanese Patent Application No. 2018-013432 filed on Jan. 30, 2018. Each of the above applications is hereby expressly incorporated by reference, in its entirety, into the present application.

BACKGROUND OF THE INVENTION

Technical Field

The present disclosure relates to an interlobar membrane display apparatus, a method, and a program that display an interlobar membrane between lung lobes in a three-dimensional image including a lung.

Related Art

In recent years, with advances in medical devices such as a computed tomography (CT) device and a magnetic resonance imaging (MRI) device, a three-dimensional image having high quality and high resolution has been used for image diagnosis. Here, since a three-dimensional image is formed of a large number of two-dimensional images and has a large amount of information, it may take time for a doctor to find a desired observation part and to perform diagnosis. Therefore, efficient diagnosis has been attempted by improving the visibility of a whole organ or a lesion. For that purpose, maximum intensity projection (MIP) display is performed through recognizing an organ of interest and extracting the organ of interest from a three-dimensional image including the organ of interest using methods, for example, a MIP method and a minimum intensity projection (MinIP) method, or volume rendering (VR) display of a three-dimensional image is performed.

On the other hand, the lung is anatomically divided into five lung lobes in total of right and left. The left lung is divided into upper and lower lobes by a major fissure as a boundary, and the right lung is divided into an upper lobe, a middle lobe, and a lower lobe by a major fissure and a minor fissure as boundaries. In the interlobar fissures, there is an interlobar membrane that separates the lung lobes. Blood vessels and bronchi inside the lungs run independently in each lung lobe. Therefore, in a case where a surgical operation is performed on a pulmonary disease such as lung cancer, a surgical technique of removing the one entire lung lobe including the disease is adopted. In adopting such a technique, it is necessary to accurately divide the lung lobe before the operation. For this reason, various methods have been proposed for dividing a lung lobe in a three-dimensional image. For example, JP2008-142481A proposes a method of extracting an interlobar fissure running between lung lobes from a CT image and dividing the lung into lung lobe units using the extracted interlobar fissure as a boundary. JP2014-161388A proposes a method of extracting a planar area from a three-dimensional image of a lung of a subject and specifying an interlobar surface by assigning, to the planar area, identification information according to a maximum principal curvature direction vector of a pixel constituting the extracted planar area.

By the way, although a lung field area is divided into five lung lobes as described above, lobulation failure may occur in which the lung lobes are not completely divided. In a case where lobulation failure occurs, the interlobar membrane is not present in a part of the interlobar fissure, and the lung lobes are connected to each other in the part where the interlobar membrane is not present. Therefore, in the part where the lung lobes are connected to each other, blood vessels and bronchi run across the lung lobes. Lobulation failure occurs near the mediastinum in the lung field area. Since the methods disclosed in JP2008-142481A and JP2014-161388A do not consider lobulation failure, it is not possible to specify whether or not lobulation failure occurs in the lung.

In order to confirm such lobulation failure, there is proposed a method in which an area having no interlobar membrane is specified and displayed by extracting a lung field area from a CT image, specifying a candidate area between lobes by detecting a boundary of the lung field area, comparing an interlobar area estimated by analyzing the CT image with the specified candidate area between the lobes (U.S. Pat. No. 9,014,445B).

By the way, the method disclosed in U.S. Pat. No. 9,014,445B needs to actually specify the interlobar membrane in a three-dimensional image. Here, in a case of the CT image, air present in the lung field has a relatively high concentration (low CT value), and the interlobar membrane has a relatively low concentration (high CT value). For this reason, by detecting a plane area having a relatively low concentration of the lung field in the CT image, the interlobar membrane can be specified. However, since the CT image has a low resolution in a body axial direction of a human body, the method disclosed in U.S. Pat. No. 9,014,445B may not be able to accurately specify the interlobar membrane. Unless the interlobar membrane can be accurately specified in this way, it is not possible to specify the area having no interlobar membrane and display an image of the lung field. In addition, since the method disclosed in U.S. Pat. No. 9,014,445B needs to compare the specified interlobar membrane with the estimated interlobar membrane, an operation cost for the comparing is required.

SUMMARY OF THE INVENTION

The present disclosure has been made in view of the above circumstances, and an object thereof is to enable simple and accurate display of an interlobar membrane.

An interlobar membrane display apparatus according to the present disclosure comprises: an interlobar position specifying unit that specifies an interlobar position in a lung field area included in a three-dimensional image; an expansion unit that expands a plane area at the interlobar position in a thickness direction to generate an expansion area including an interlobar membrane; a projection processing unit that processes the expansion area by a projection method that emphasizes the interlobar membrane to generate a projection image; and a display control unit that displays the projection image on a display unit.

In the interlobar membrane display apparatus according to the present disclosure, the expansion unit may expand the plane area at the interlobar position until a distance between the expansion area and a blood vessel, a bronchus, or a lesion in the lung field area is a predetermined interval.

In the interlobar membrane display apparatus according to the present disclosure, in a case where the three-dimensional image is a CT image, the projection processing unit may generate the projection image by a maximum intensity projection method.

In the interlobar membrane display apparatus according to the present disclosure, the expansion unit may expand the plane area at the interlobar position in the thickness direction by dilation processing.

In the interlobar membrane display apparatus according to the present disclosure, the interlobar position specifying unit may separate the lung field area into lung lobes and specify a boundary between the separated lung lobes as the interlobar position.

In the interlobar membrane display apparatus according to the present disclosure, the interlobar position specifying unit may detect an interlobar fissure in the lung field area and specify a position of the detected interlobar fissure as the interlobar position.

An interlobar membrane display method according to the present disclosure comprises: specifying an interlobar position in a lung field area included in a three-dimensional image; expanding a plane area at the interlobar position in a thickness direction to generate an expansion area including an interlobar membrane; processing the expansion area by a projection method that emphasizes the interlobar membrane to generate a projection image; and displaying the projection image on a display unit.

The interlobar membrane display method according to the present disclosure may be provided as a program for causing a computer to execute the method.

Another interlobar membrane display apparatus according to the present disclosure comprises: a memory that stores instructions for causing a computer to perform execution; and a processor configured to execute the stored instructions, in which the processor executes processing of specifying an interlobar position in a lung field area included in a three-dimensional image, expanding a plane area at the interlobar position in a thickness direction to generate an expansion area including an interlobar membrane, processing the expansion area by a projection method that emphasizes the interlobar membrane to generate a projection image, and displaying the projection image on a display unit.

According to the present disclosure, an interlobar position in a lung field area included in a three-dimensional image is specified, and a plane area at the interlobar position is expanded in a thickness direction and an expansion area including an interlobar membrane is generated. The expansion area generated in this manner includes the interlobar membrane. Here, in the three-dimensional image, the interlobar membrane has a signal value different from that of the surrounding tissue. Therefore, by processing the expansion area by a projection method that emphasizes the interlobar membrane to generate a projection image, and displaying the generated projection image, the projection image in which the interlobar membrane is reliably included and the interlobar membrane is emphasized is displayed. Thereby, it is possible to accurately display the interlobar membrane with a simple operation. In addition, since the projection image reliably includes the interlobar membrane, it is possible to accurately specify a position where lobulation failure occurs in the projection image.

DETAILED DESCRIPTION

Figure 1:
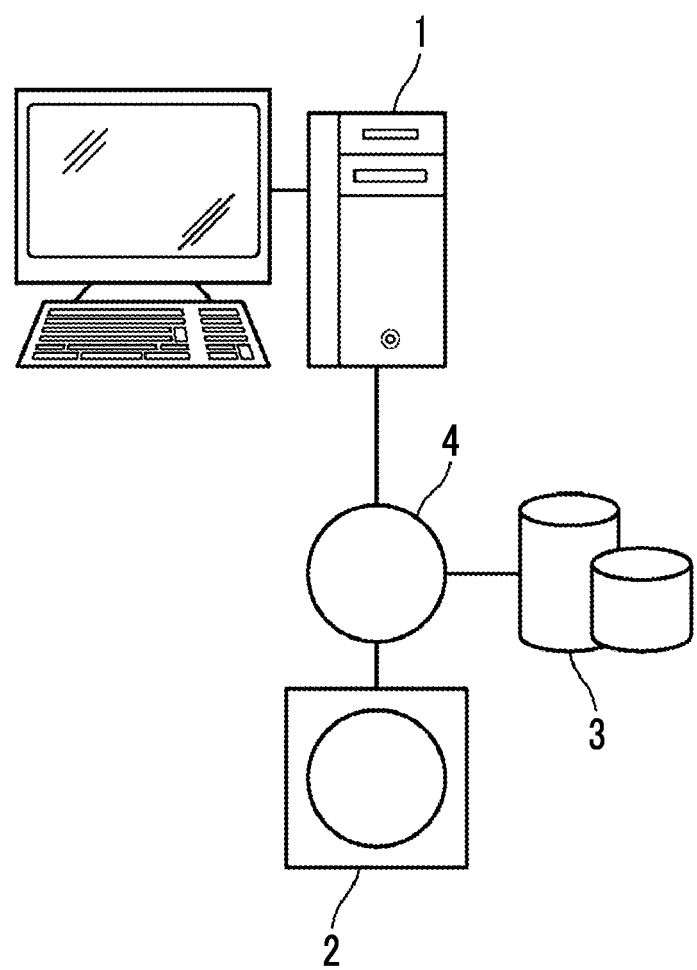
FIG. 1 is a hardware configuration diagram showing an outline of a diagnosis support system to which an interlobar membrane display apparatus according to an embodiment of the present disclosure is applied.

Hereinafter, embodiments of the present disclosure will be described with reference to the drawings. FIG. 1 is a hardware configuration diagram showing an outline of a diagnosis support system to which an interlobar membrane display apparatus according to an embodiment of the present disclosure is applied. As shown in FIG. 1, in the diagnosis support system, an interlobar membrane display apparatus 1, a three-dimensional image capturing apparatus 2, and an image storage server 3 according to the present embodiment are connected in a communicable state via a network 4. Therefore, in the diagnosis support system, processing of acquiring a three-dimensional image of the chest of a subject and displaying an interlobar membrane included in a lung field is performed.

The three-dimensional image capturing apparatus 2 is an apparatus that images a part of the subject to be diagnosed and generates a three-dimensional image representing the part, and specifically, a CT apparatus, an MM apparatus, and a positron emission tomography (PET) apparatus. A three-dimensional image generated by the three-dimensional image capturing apparatus 2 is transmitted to the image storage server 3 and stored. In the present embodiment, in order to perform processing of displaying the interlobar membrane included in the lung field, the diagnosis target part of the subject is set to the chest including the lung field. The three-dimensional image capturing apparatus 2 is a CT apparatus, and the three-dimensional image capturing apparatus 2 generates a three-dimensional image consisting of a plurality of axial cross-sectional tomographic images of the chest of the subject.

The image storage server 3 is a computer that stores and manages various kinds of data, and comprises a large-capacity external storage device and database management software. The image storage server 3 communicates with other devices via a wired or wireless network 4 to transmit and receive image data and the like. Specifically, image data such as a three-dimensional image generated by the three-dimensional image capturing apparatus 2 is acquired via a network, and stored and managed in a recording medium such as a large-capacity external storage device. The storage format of the image data and the communication between the apparatuses via the network 4 are based on a protocol such as Digital Imaging and Communication in Medicine (DICOM). In the present embodiment, a three-dimensional image of the chest of the subject is stored in the image storage server 3.

The interlobar membrane display apparatus 1 has an interlobar membrane display program of the present disclosure installed in one computer. The computer may be a workstation or a personal computer directly operated by a doctor performing diagnosis, or may be a server computer connected to them via a network. The interlobar membrane display program is recorded on a recording medium such as a digital versatile disc (DVD) or a compact disc read only memory (CD-ROM) and distributed, and is installed in a computer from the recording medium. Alternatively, it is stored in a storage device of a server computer connected to a network or a network storage in a state where it can be accessed from the outside, and is downloaded and installed on a computer used by a doctor in response to a request.

Figure 2:
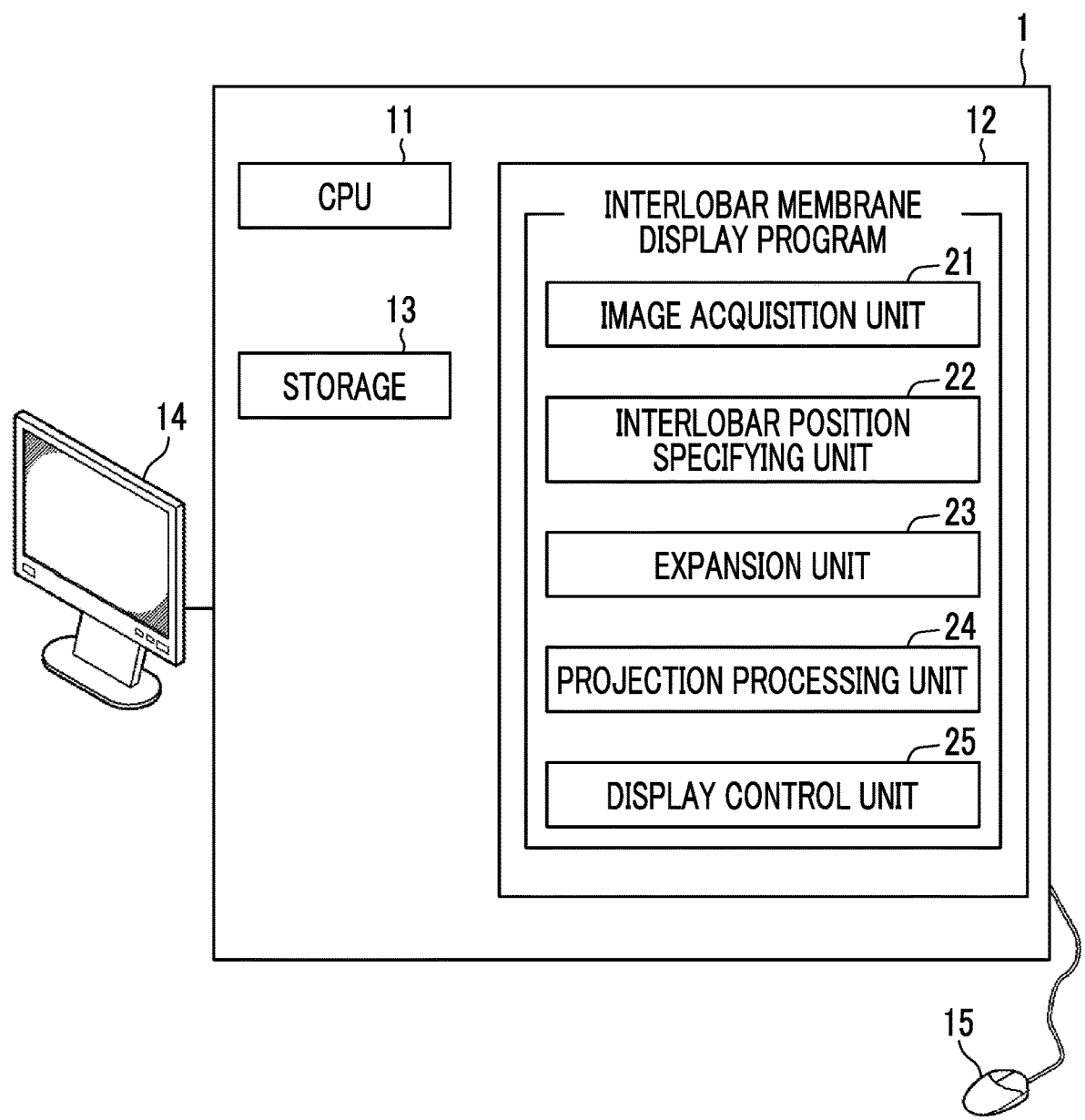
FIG. 2 is a diagram showing a schematic configuration of the interlobar membrane display apparatus.

FIG. 2 is a diagram showing a schematic configuration of an interlobar membrane display apparatus realized by installing an interlobar membrane display program in a computer. As shown in FIG. 2, the interlobar membrane display apparatus 1 comprises a central processing unit (CPU) 11, a memory 12, and a storage 13 as a standard work station configuration. In addition, a display 14 such as a liquid crystal display, and an input unit 15 such as a keyboard and a mouse are connected to the interlobar membrane display apparatus 1. The display 14 corresponds to a display unit.

The storage 13 consists of a storage device such as a hard disk or a solid state drive (SSD). The storage 13 stores a three-dimensional image of the subject and various kinds of information including information necessary for processing, which are acquired from the image storage server 3 via the network 4.

The memory 12 stores an interlobar membrane display program. An interlobar membrane display program specifies, as processing to be executed by the CPU 11, image acquisition processing of acquiring a three-dimensional image, interlobar position specifying processing of specifying an interlobar position in a lung field area included in a three-dimensional image, expansion processing of expanding a plane area at the interlobar position in a thickness direction to generate an expansion area including an interlobar membrane, projection processing of processing the expansion area by a projection method that emphasizes the interlobar membrane to generate a projection image, and display control processing displaying the projection image on the display 14.

Then, in a case where the CPU 11 executes these processing items according to the program, the computer functions as an image acquisition unit 21, an interlobar position specifying unit 22, an expansion unit 23, a projection processing unit 24, and a display control unit 25. In the present embodiment, the CPU 11 executes the function of each unit according to the interlobar membrane display program. However, in addition to the CPU 11, a programmable logic device (PLD) that is a processor of which a circuit configuration can be changed after manufacturing such as a field programmable gate array (FPGA) can be used as a general-purpose processor that executes software and functions as various processing units. In addition, processing of each unit may be executed by a dedicated electric circuit that is a processor having a circuit configuration designed to be dedicated to execute specific processing, such as an application specific integrated circuit (ASIC).

One processing unit may be constituted by one of these various processors, or may be a combination of two or more processors of the same type or different types (for example, a combination of a plurality of FPGAs or a combination of a CPU and an FPGA). A plurality of processing units may be constituted by one processor. As an example in which the plurality of processing units are constituted by one processor, first, as represented by a computer such as a client or a server, one processor is constituted by a combination of one or more CPUs and software and this processor functions as the plurality of processing units. Second, as represented by a system on chip (SoC), a processor that realizes the functions of the entire system including the plurality of processing units by using one integrated circuit (IC) chip is used. As described above, the various processing units are constituted by using one or more of the above described various processors as a hardware structure.

The hardware structure of these various processors is more specifically an electric circuit (circuitry) in which circuit elements such as semiconductor elements are combined.

The image acquisition unit 21 acquires a three-dimensional image V0 of the subject from the image storage server 3. In a case where the three-dimensional image V0 is already stored in the storage 13, the three-dimensional image V0 may be acquired from the storage 13.

The interlobar position specifying unit 22 specifies an interlobar position in a lung field area included in the three-dimensional image V0. As a method of specifying an interlobar position, for example, the method disclosed in U.S. Pat. No. 9,014,445B may be used. The method disclosed in U.S. Pat. No. 9,014,445B is a method of extracting a lung field area from the three-dimensional image V0, registering the extracted lung field area and a standard lung model, separating the lung field area into lung lobes, and using a boundary between the separated lung lobes as the interlobar position. As a method of extracting a lung field area, a method may be used in which a voxel value (that is, a CT value) of each voxel of the three-dimensional image V0 is binarized using a threshold value for separating a lung field and other areas from each other, and labeling processing is performed on the binarized data acquired by the binarization processing, and then, by using the label image data obtained in this manner, a label area having a maximum volume is extracted, the extracted area is filled, and unnecessary area such as a bronchus is removed to extract a lung field area.

Figure 3:
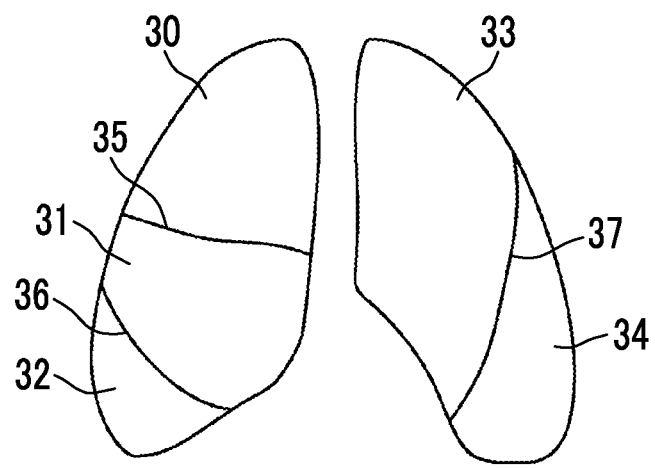
FIG. 3 is a schematic diagram showing an interlobar position specified in a lung field area.

FIG. 3 is a schematic diagram showing an interlobar position specified in a lung field area. In FIG. 3, the lung on the left side as viewed from the front is the right lung in the human body, and the lung on the right side as viewed from the front is the left lung in the human body. As shown in FIG. 3, in the human body, the right lung is divided into three lung lobes of an upper lobe 30, a middle lobe 31, and a lower lobe 32, and the left lung is divided into two areas of an upper lobe 33 and a lower lobe 34. Therefore, as shown in FIG. 3, two interlobar positions 35 and 36 are specified in the right lung, and one interlobar position 37 is specified in the left lung. The interlobar positions 35 to 37 are specified as an area having a thickness of one pixel on the three-dimensional image V0.

A method of specifying an interlobar position is not limited to the above method. For example, the method disclosed in JP2008-142481A may be used in which an interlobar fissure in a lung field area is detected, and the position of the detected interlobar fissure is specified as an interlobar position may be used. Further, the method disclosed in JP2014-161388A may be used in which a planar area is extracted from a three-dimensional image of the lung, and an interlobar surface is specified as an interlobar position by assigning, to the planar area, identification information according to a maximum principal curvature direction vector of a pixel constituting the extracted planar area.

The expansion unit 23 expands a plane area at the interlobar position in a thickness direction to generate an expansion area including an interlobar membrane. Although the three interlobar positions 35 to 37 are specified in the lung field area, processing of generating the expansion area is the same at any of the interlobar positions. Therefore, here, only generation of the expansion area at the interlobar position 35 between the upper lobe 30 and the middle lobe 31 of the right lung among the specified interlobar positions 35 to 37 will be described.

Figure 4:
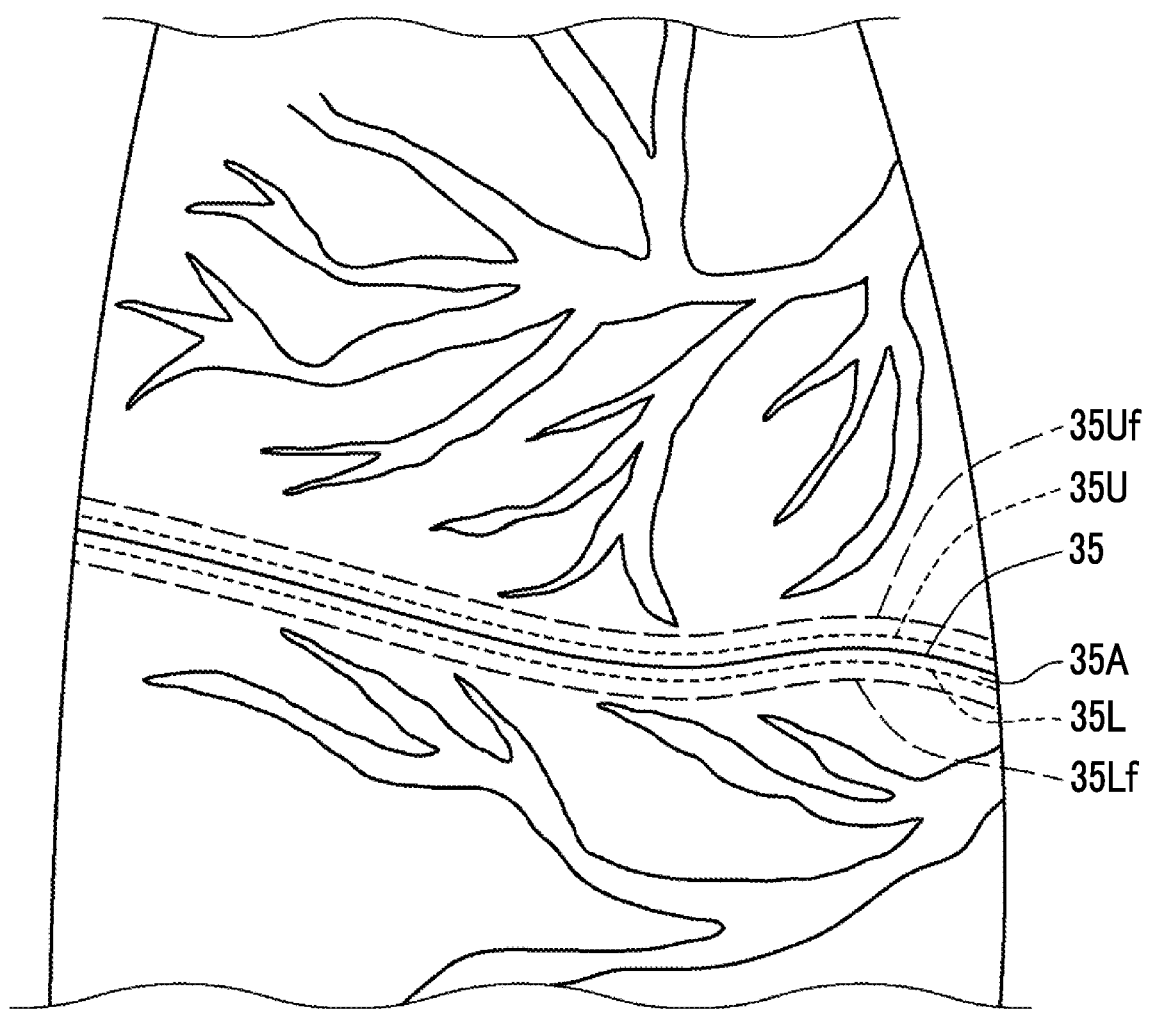
FIG. 4 is a diagram for explaining generation of an expansion area.
Figure 5:
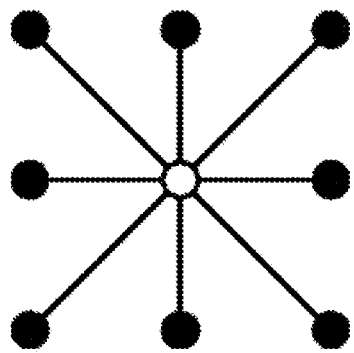
FIG. 5 is a diagram showing structural elements of dilation processing.

FIG. 4 is a diagram for explaining generation of an expansion area. In FIG. 4, a peripheral area of the interlobar position 35 in a coronal cross section of the right lung in the lung field area is shown in an enlarged manner, and the interlobar position 35 is indicated by a solid line having a thickness of one pixel. In FIG. 4, a right-left direction corresponds to a right-left direction of the human body. In the present embodiment, the plane area at the interlobar position 35 is expanded in a thickness direction by dilation processing. Dilation processing is processing of searching for a maximum value within a predetermined width centered on a target pixel on the interlobar position 35 by using structural elements as shown in FIG. 5. By performing dilation processing using structural elements shown in FIG. 5 once, the plane area at the interlobar position 35 is expanded by one pixel in a thickness direction thereof (vertical direction shown in FIG. 4) to generate an expansion area 35A. An upper surface 35U and a lower surface 35L of the expansion area 35A in a case where the plane area at the interlobar position 35 is expanded are indicated by short broken lines in FIG. 4.

In the present embodiment, the plane area at the interlobar position 35 is expanded by dilation processing until a distance between the upper surface 35U or the lower surface 35L of the expansion area 35A and a blood vessel, a bronchus, or a lesion such as cancer in the lung field area is a predetermined interval. Here, since the three-dimensional image V0 is a CT image, air in the lung field area is represented by a high concentration (low CT value), and a blood vessel, a bronchus, and a lesion are represented by a low concentration (high CT value). On the other hand, an interlobar membrane at a boundary of the lung field has a lower concentration than air in a three-dimensional image, but has a higher concentration than a blood vessel, a bronchus, and a lesion. An interlobar membrane is a continuous area near the interlobar position, whereas a blood vessel, a bronchus, and a lesion are discontinuous areas in a case of being viewed in relation to the interlobar membrane.

The expansion unit 23 repeats dilation processing until the upper surface 35U or the lower surface 35L of the expansion area 35A comes into contact with a discontinuous structure having a concentration lower than a predetermined threshold value Th1, that is, a blood vessel, a bronchus, or a lesion. As the threshold value Th1, a value larger than a CT value of an interlobar membrane is used. In a case where the upper surface 35U or the lower surface 35L of the expansion area 35A comes into contacts with a blood vessel, a bronchus, or a lesion, the expansion unit 23 specifies the expansion area 35A generated by previous dilation processing as the final expansion area 35A. An upper surface 35Uf and a lower surface 35Lf of the final expansion area 35A are indicated by long broken lines in FIG. 4.

An interval between the upper surface 35Uf or the lower surface 35Lf of the finally generated expansion area 35A and a blood vessel, a bronchus, or a lesion varies depending on the size of the structural elements used in dilation processing. In the present embodiment, the expansion area 35A is vertically enlarged by one pixel by the structural elements used for dilation processing. For this reason, the interval between the upper surface 35Uf or the lower surface 35Lf of the finally generated expansion area 35A and a blood vessel, a bronchus, or a lesion is one pixel. Therefore, in the present embodiment, a plane area at an interlobar position is expanded by dilation processing until a distance between the upper surface 35Uf or the lower surface 35Lf of the expansion area 35A and a blood vessel, a bronchus, or a lesion is an interval of one pixel.

Figure 6:
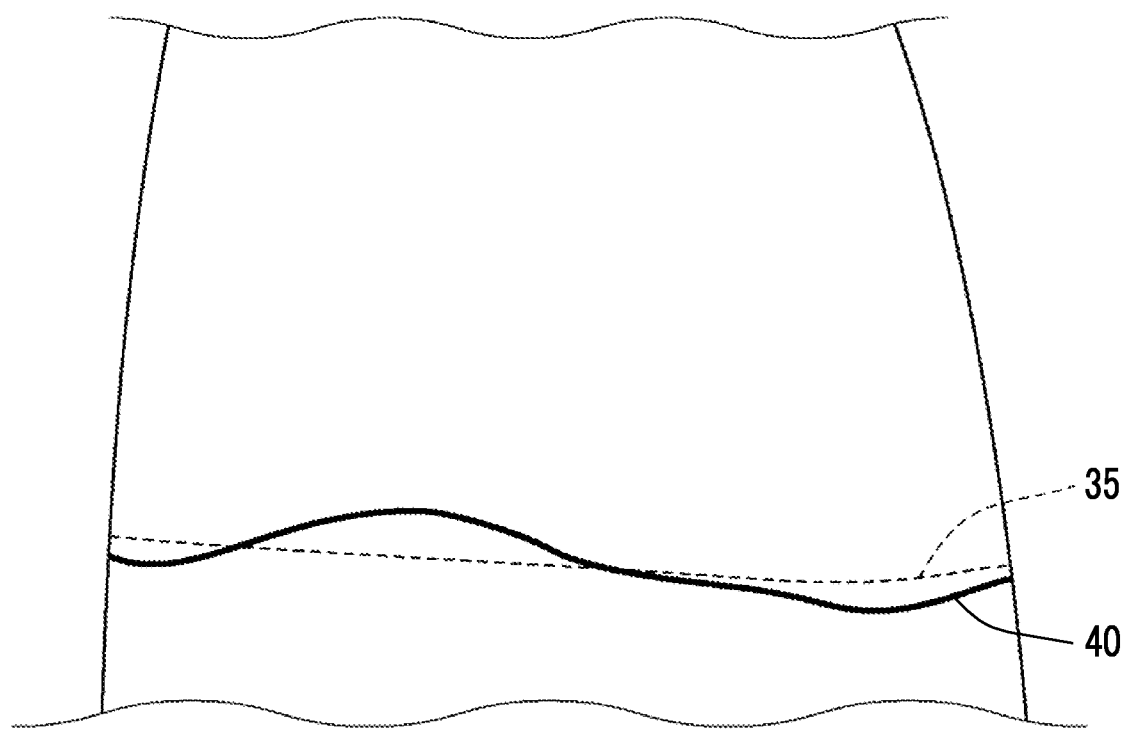
FIG. 6 is a diagram showing a state where an interlobar membrane is present.
Figure 7:
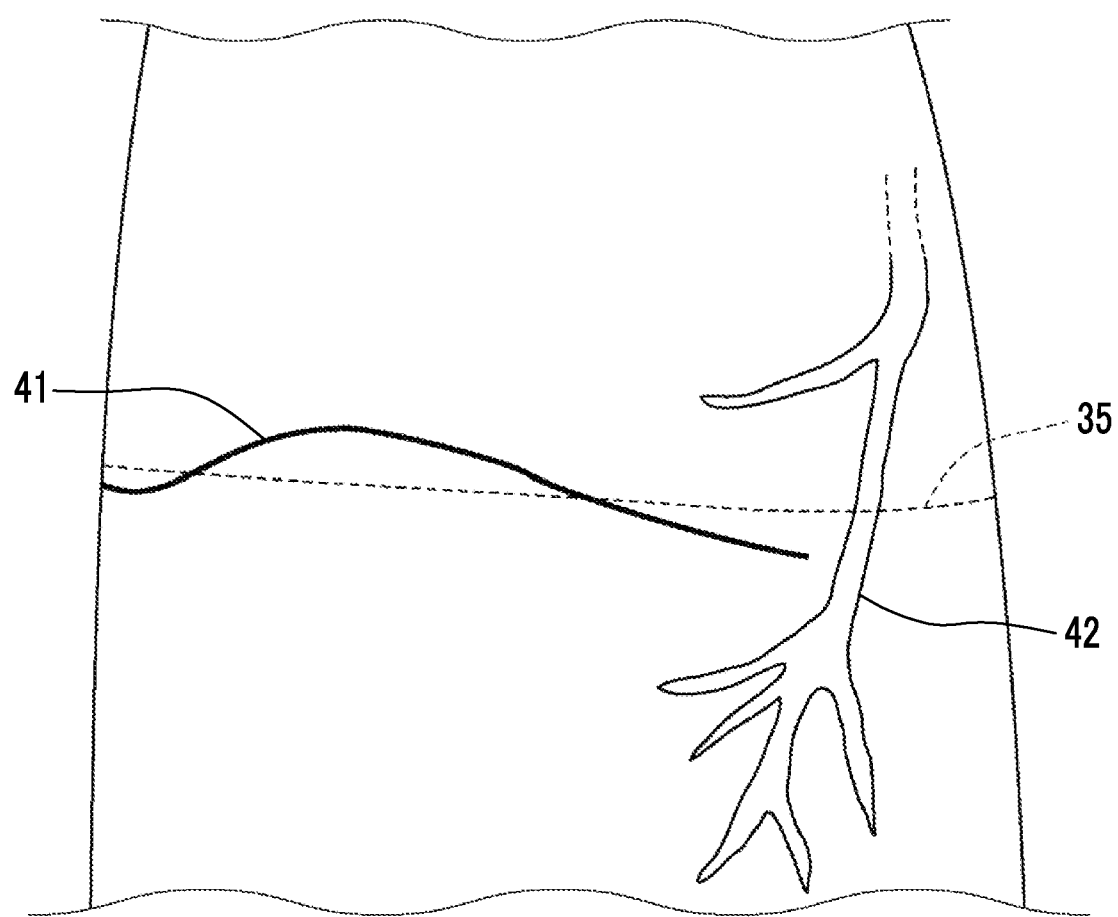
FIG. 7 is a diagram showing a state where an interlobar membrane is present in a case of lobulation failure.

On the other hand, the specified interlobar position 35 may not match the position of an interlobar membrane. For example, as shown in FIG. 6, in a case where an interlobar membrane 40 is present and the interlobar position 35 is specified as indicated by a broken line, the interlobar position 35 does not match the position of the interlobar membrane 40. In addition, as shown in FIG. 7, in a case where an interlobar membrane 41 is not present over the entire area between the lobes due to lobulation failure, the position of the interlobar membrane 41 cannot be accurately specified even though the specified interlobar position 35 is used. FIG. 7 shows that a bronchus 42 is present between the lung lobes due to lobulation failure.

Figure 8:
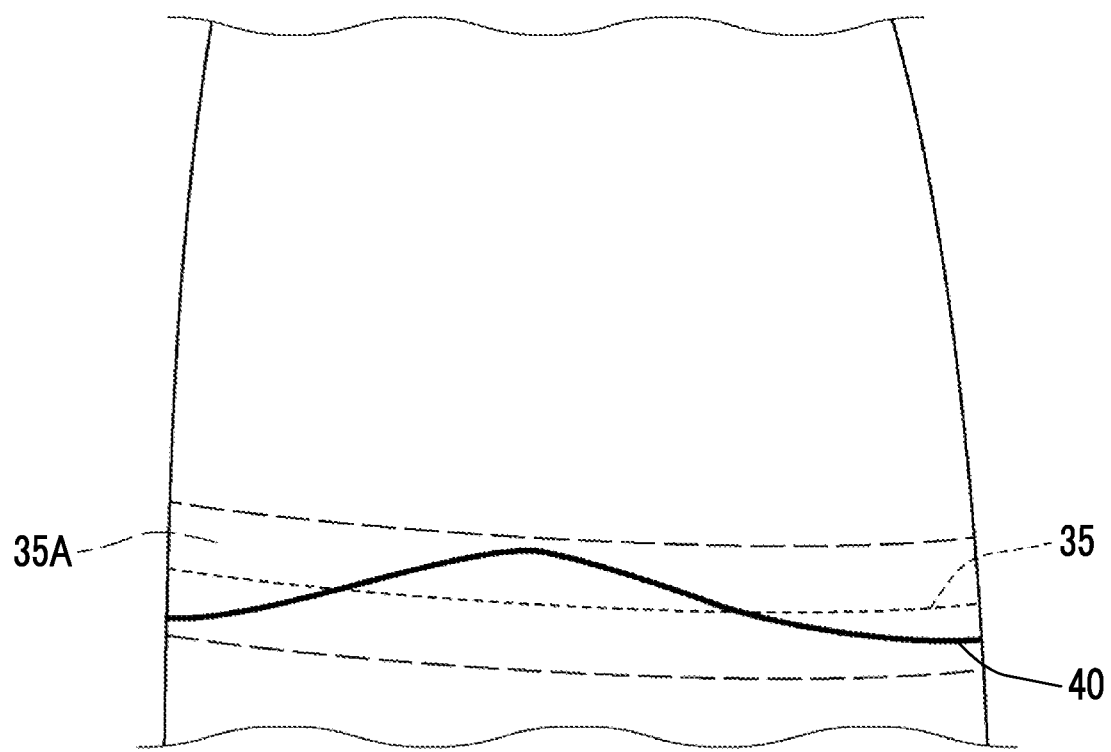
FIG. 8 is a diagram showing the expansion area.
Figure 9:
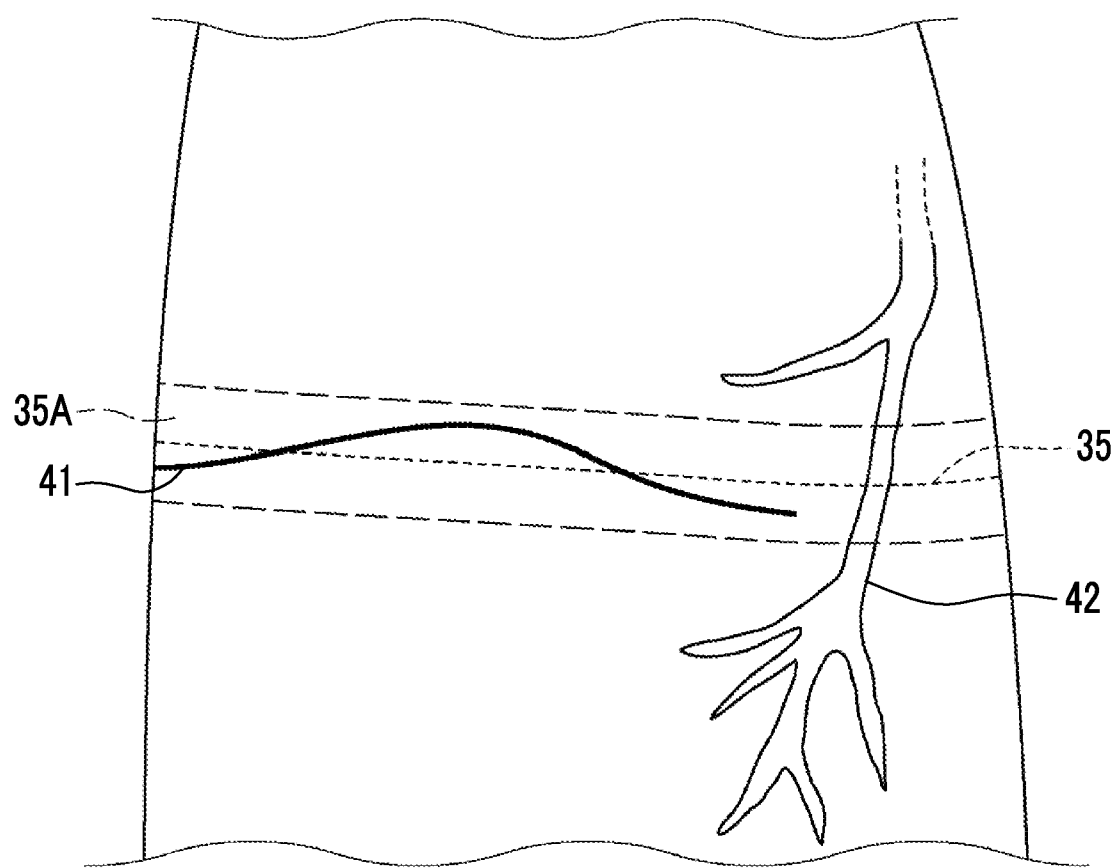
FIG. 9 is a diagram showing an expansion area in a case of lobulation failure.

In the present embodiment, the expansion unit 23 expands a plane area at an interlobar position to generate the expansion area 35A. Therefore, even though the interlobar position 35 does not match the position of the interlobar membrane 40 as shown in FIG. 6, the generated expansion area 35A includes the interlobar membrane 40 as shown in FIG. 8. In addition, even though lobulation failure occurs as shown in FIG. 7, the generated expansion area 35A includes the interlobar membrane 41 that does not completely separate lobes as shown in FIG. 9.

Figure 10:
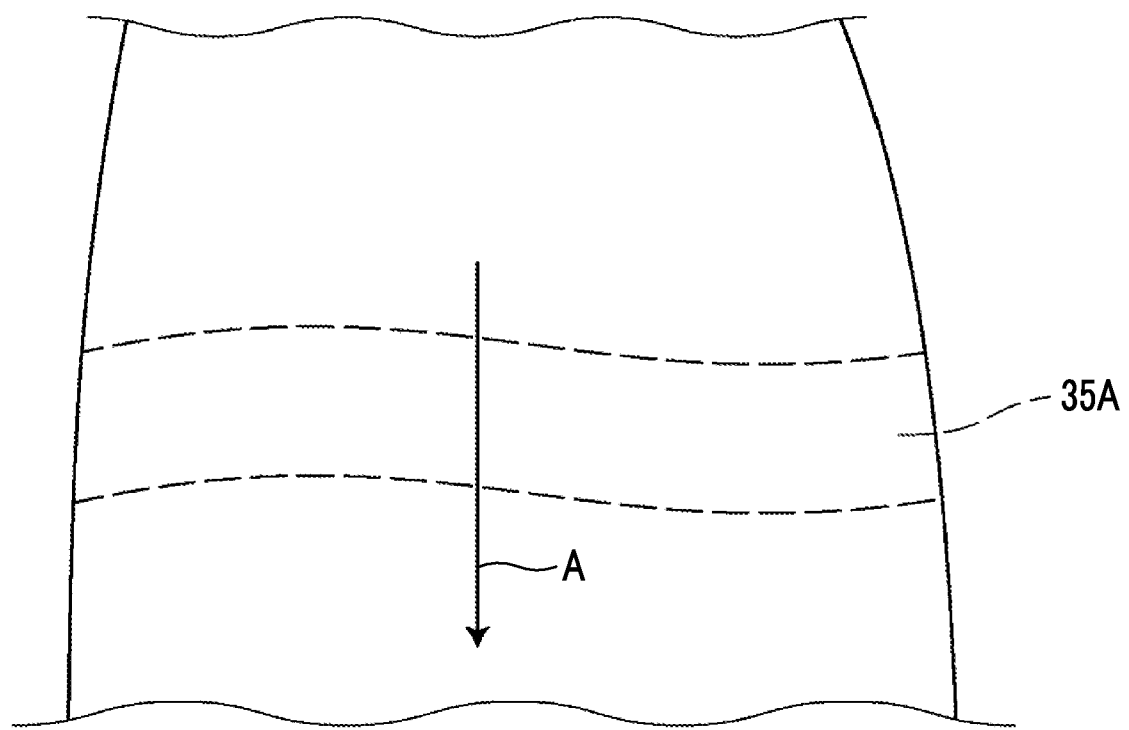
FIG. 10 is a diagram showing a projection direction in a case where a projection image is generated.

The projection processing unit 24 processes the expansion area 35A by a projection method that emphasizes the interlobar membrane to generate a projection image. FIG. 10 is a diagram for explaining generation of a projection image. As shown in FIG. 10, in the present embodiment, since the three-dimensional image V0 is a CT image, a projection image is generated by projecting an expansion area by a maximum intensity projection method in a direction of an arrow A intersecting between the lobes.

Figure 11:
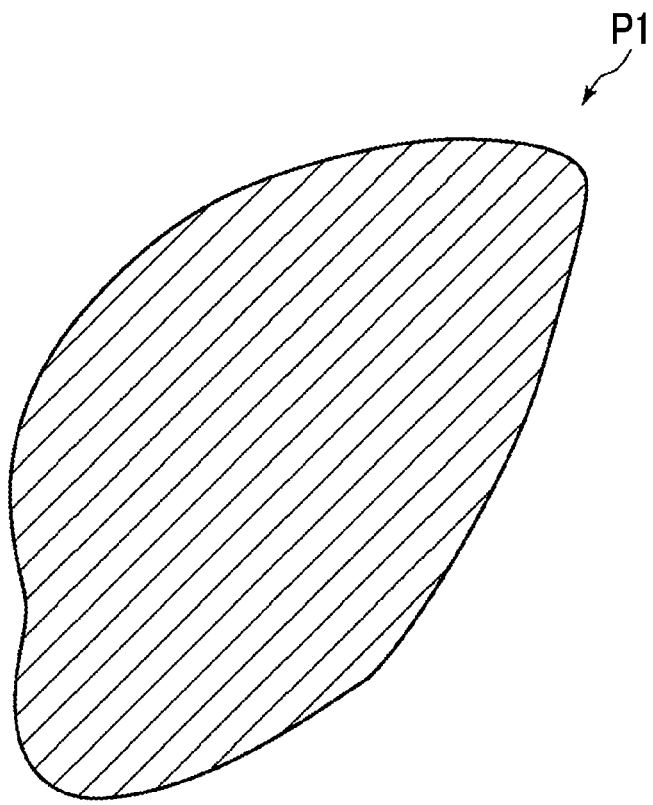
FIG. 11 is a diagram showing the projection image.
Figure 12:
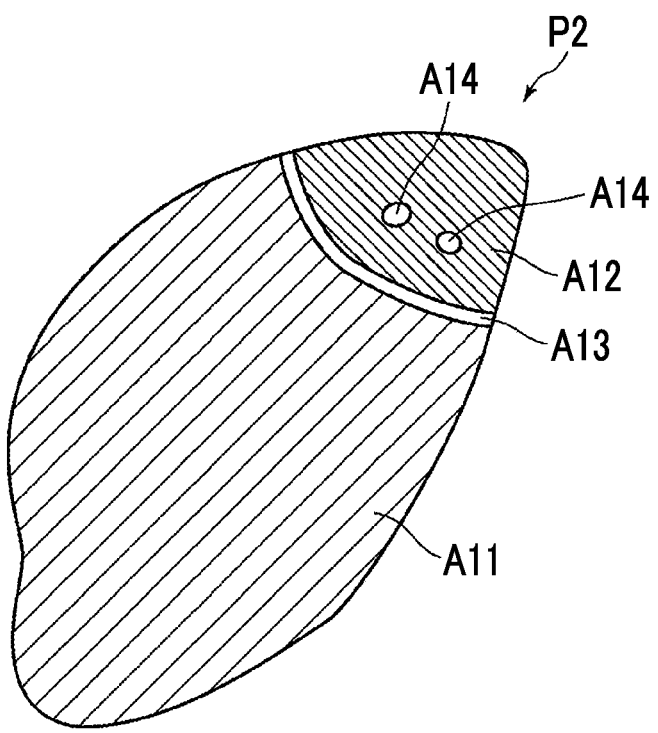
FIG. 12 is a diagram showing a projection image in a case of lobulation failure.

In the present embodiment, the expansion area 35A includes an interlobar membrane and a lung field area. A voxel value of the lung field area is smaller than a voxel value of the interlobar membrane. Therefore, in a case where an interlobar membrane is present over the entire area between the lobes as shown in FIG. 8, a projection image P1 generated by a maximum intensity projection method is an image having voxel values of the interlobar membrane over the entire area as shown in FIG. 11. On the other hand, in a case where lobulation failure occurs as shown in FIG. 9, a projection image P2 generated by a maximum intensity projection method includes an area A11 in which an interlobar membrane is present and an area A12 in which an interlobar membrane is not present as shown in FIG. 12. Here, since the area A11 in which an interlobar membrane is present has a lower concentration image than the area A12 in which an interlobar membrane is not present, in the projection image P2, the area A11 in which an interlobar membrane is present can be distinguished from the area A12 in which an interlobar membrane is not present.

A boundary between the area A11 in which an interlobar membrane is present and the area A12 in which an interlobar membrane is not present exhibits a lower concentration due to the dense tissue of the interlobar membrane, and as a result, at the boundary between the area A11 and the area A12, a line A13 having a lower concentration than the area A11 of the interlobar membrane appears. Presence of the line A13 makes it possible to more clearly distinguish the area A11 in which an interlobar membrane is present from the area A12 in which an interlobar membrane is not present. In the area A12 in which an interlobar membrane is not present, a blood vessel and a bronchus run between the lung lobes. In addition, a lesion may be present between the lung lobes. Here, a blood vessel, a bronchus, or a lesion has a lower concentration than an interlobar membrane. Therefore, the area A12 includes an area A14 of a blood vessel, a bronchus, or a lesion having a low concentration.

The display control unit 25 displays the projection image on the display 14.

Figure 13:
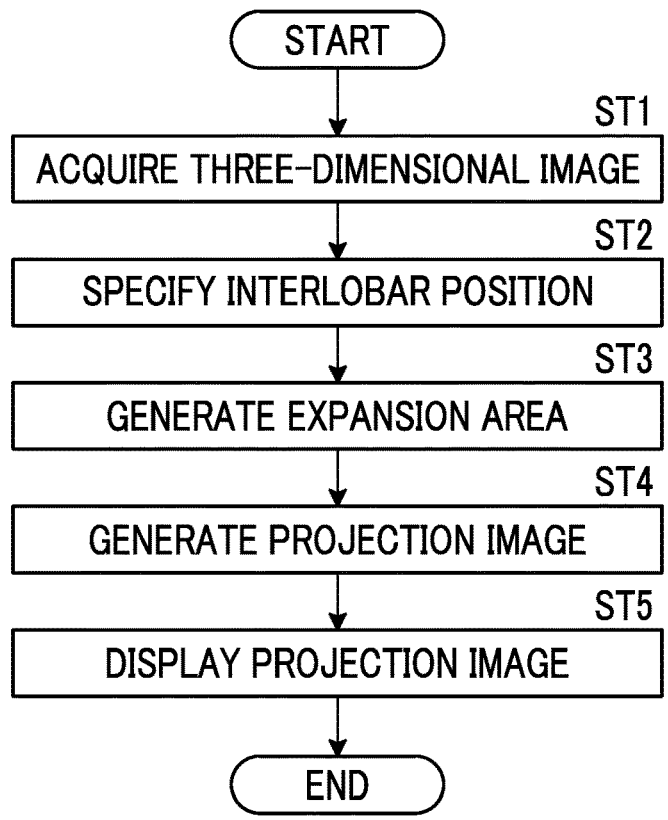
FIG. 13 is a flowchart showing processing performed in the present embodiment.

Next, processing performed in the present embodiment will be described. FIG. 13 is a flowchart showing processing performed in the present embodiment. First, the image acquisition unit 21 acquires the three-dimensional image V0 (step ST1), and the interlobar position specifying unit 22 specifies an interlobar position in a lung field area included in the three-dimensional image V0 (step ST2). Next, the expansion unit 23 expands a plane area at the interlobar position in a thickness direction to generate an expansion area including an interlobar membrane (step ST3), and the projection processing unit 24 processes the expansion area 35A by a projection method that emphasizes the interlobar membrane to generate a projection image (step ST4). Then, the display control unit 25 displays the projection image on the display 14 (step ST5), and the processing is ended.

As described above, according to the present embodiment, since the plane area at the interlobar position 35 is expanded in a thickness direction to generate the expansion area 35A, the generated expansion area 35A includes an interlobar membrane. Here, in the three-dimensional image V0, the interlobar membrane has a signal value different from that of the surrounding tissue. Therefore, by processing the expansion area 35A by a projection method that emphasizes the interlobar membrane, for example, a maximum intensity projection method, to generate a projection image, and displaying the generated projection image, the projection image in which the interlobar membrane is reliably included and the interlobar membrane is emphasized can be displayed. Therefore, it is possible to accurately display the interlobar membrane with a simple operation. In addition, since the projection image reliably includes the interlobar membrane, it is possible to accurately specify a position where lobulation failure occurs in the projection image.

Figure 14:
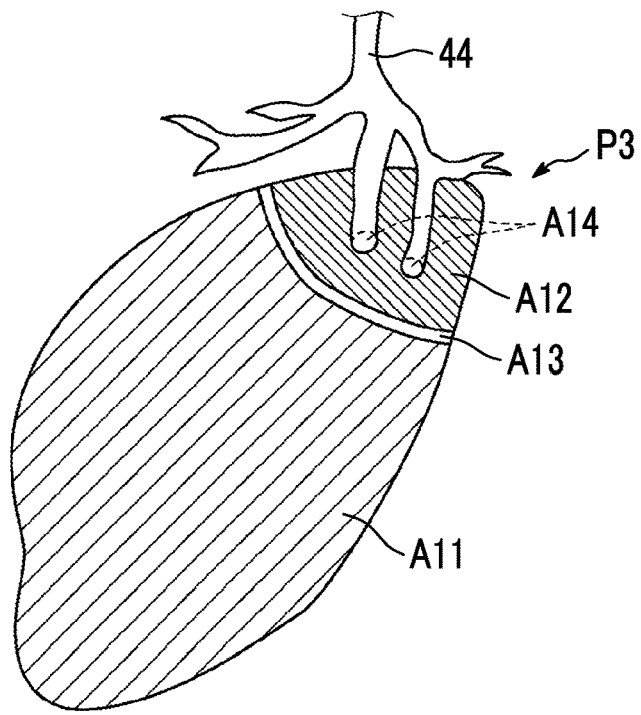
FIG. 14 is a diagram showing a projection image on which a bronchus is superimposed.

In the above embodiment, although the projection image is displayed on the display 14, a blood vessel or a bronchus may be displayed so as to be superimposed on the projection image. FIG. 14 is a diagram showing a projection image on which a bronchus is superimposed. As shown in FIG. 14, similarly to the projection image P2 shown in FIG. 12, a projection image P3 includes the area A11 in which an interlobar membrane is present, the A12 in which an interlobar membrane is not present, the line A13 at the boundary between the area A11 and the area A12, and the area A14 of a blood vessel, a bronchus, or a lesion. In a case where a blood vessel or a bronchus is superimposed on the projection image in this way, the blood vessel or the bronchus may be displayed using volume rendering. In FIG. 14, the bronchus 44 displayed using volume rendering runs through the area A14. This makes it possible to easily observe a running state of an interlobar membrane and a blood vessel or a bronchus, or a state where a lesion is present.

Further, in the above embodiment, a CT image is used as the three-dimensional image V0, but the present invention is not limited to this, and an MM image or a PET image may be used as the three-dimensional image V0. In this case, projection processing of emphasizing an interlobar membrane may be appropriately selected according to the type of an image.

What is claimed is:

1. An interlobar membrane display apparatus comprising at least one processor, wherein the processor is configured to:
   specify an interlobar position in a lung field area included in a three-dimensional image;
   extend a plane area at the interlobar position in a thickness direction to generate an expansion area including an interlobar membrane, wherein the thickness direction is a vertical direction with respect to the plane area at the interlobar position;
   process the expansion area by a projection method that emphasizes the interlobar membrane to generate a projection image; and
   display the projection image on a display, and
   expand the plane area at the interlobar position until a distance between the expansion area and a blood vessel, a bronchus, or a lesion in the lung field area is a predetermined interval.

2. The interlobar membrane display apparatus according to claim 1,
   wherein, in a case where the three-dimensional image is a CT image, the processor is configured to generate the projection image by a maximum intensity projection method.

3. The interlobar membrane display apparatus according to claim 1,
   wherein the processor is configured to expand the plane area at the interlobar position in the thickness direction by dilation processing.

4. The interlobar membrane display apparatus according to claim 1,
   wherein the processor is configured to separate the lung field area into lung lobes and specifies a boundary between the separated lung lobes as the interlobar position.

5. The interlobar membrane display apparatus according to claim 1,
   wherein the processor is configured to detect an interlobar fissure in the lung field area and specifies a position of the detected interlobar fissure as the interlobar position.

6. The interlobar membrane display apparatus according to claim 1,
   wherein the expansion area comprises a first area located above the interlobar position and a second area located below the interlobar position.

7. An interlobar membrane display method comprising:
   specifying an interlobar position in a lung field area included in a three-dimensional image;
   expanding a plane area at the interlobar position in a thickness direction to generate an expansion area including an interlobar membrane until a distance between the expansion area and a blood vessel, a bronchus, or a lesion in the lung field area is a predetermined interval, wherein the thickness direction is a vertical direction with respect to the plane area at the interlobar position;

processing the expansion area by a projection method that emphasizes the interlobar membrane to generate a projection image; and displaying the projection image on a display.

8. A non-transitory computer-readable storage medium that stores an interlobar membrane display program causing a computer to execute:

a procedure of specifying an interlobar position in a lung field area included in a three-dimensional image;

a procedure of expanding a plane area at the interlobar position in a thickness direction to generate an expansion area including an interlobar membrane until a distance between the expansion area and a blood vessel, a bronchus, or a lesion in the lung field area is a predetermined interval, wherein the thickness direction is a vertical direction with respect to the plane area at the interlobar position;

a procedure of processing the expansion area by a projection method that emphasizes the interlobar membrane to generate a projection image; and a procedure of displaying the projection image on a display.

* * * * *